United States Patent [19]

Mayne et al.

[11] Patent Number: 4,745,069

[45] Date of Patent: May 17, 1988

[54] CLONING VECTORS FOR EXPRESSION OF EXOGENOUS PROTEIN

[75] Inventors: Nancy G. Mayne; J. Paul Burnett; Ramamoorthy Belegaje; Hansen M. Hsiung, all of Indianapolis, Ind.

[73] Assignee: Eli Lilly and Company, Indianapolis, Ind.

[21] Appl. No.: 586,581

[22] Filed: Mar. 6, 1984

Related U.S. Application Data

[63] Continuation-in-part of Ser. No. 381,992, May 25, 1982, abandoned.

[51] Int. Cl.[4] ............... C12N 15/00; C12N 1/20; C12P 21/00; C12P 19/34; C07H 21/02
[52] U.S. Cl. .................... 435/320; 435/68; 435/91; 435/172.1; 435/172.3; 435/253; 536/27; 935/29; 935/47; 935/48; 935/49; 935/51
[58] Field of Search ............ 435/68, 70, 91, 71, 435/172.3, 253, 317, 172.1; 536/27; 935/6, 9, 11, 12, 38, 40, 41, 47, 48, 72, 73, 29, 49, 51

[56] References Cited

U.S. PATENT DOCUMENTS

4,332,892 6/1982 Ptashne et al. ............... 435/68
4,624,926 11/1986 Inouye et al. ............... 435/253

FOREIGN PATENT DOCUMENTS

0055942 7/1982 European Pat. Off. ......... 435/172.3

OTHER PUBLICATIONS

Nakamura et al, "DNA sequence of the Serratia Marcescens Lipoprotein Gene", Proc, Natl. Acad. Sci. USA 77: 1369 (1980).

Yamagata et al, "Comparison of the Lipoprotein Gene Among the Enterobacteriaceae", J. Biol Chem. 256: 2194 (1981).

Lee et al, "Expression of the Serratia Marcescens Lipoprotein Gene in *Escherichia Coli*", J. Bacteriol, 146: 861 (1981).

Light et al, "Specificity of Bovine Enterokinase Toward Protein Substrates", Anal. Biochem. 106: 199 (1980).

*Primary Examiner*—James Martinell, Ph.D.
*Attorney, Agent, or Firm*—William C. Martens; Leroy Whitaker

[57] ABSTRACT

A recombinant DNA cloning vector useful for expressing exogenous protein is described, which comprises (a) a DNA segment containing a functional origin of replication;

(b) one or more DNA segments, each of which conveys to a transformable host cell a property useful for selection when said vector is transformed into said host cell; and (c) a DNA segment comprising a sequence that defines, in tandem, (1) the promoter of a lipoprotein expression control sequence, (2) the 5' untranslated region of a lipoprotein expression control sequence and (3) a translation start codon followed, without interposition of a portion or all of a nucleotide sequence coding for endogenous protein, by a nucleotide sequence coding for an enterokinase cleavage site to which is joined, without interruption, a nucleotide sequence coding for an exogenous protein.

26 Claims, 9 Drawing Sheets

CLONING VECTORS FOR EXPRESSION OF EXOGENOUS PROTEIN

CROSS REFERENCE

This is a continuation-in-part of application Ser. No. 381,992 filed May 25, 1982, now abandoned.

BACKGROUND OF THE INVENTION

This invention is directed to novel DNA sequences and to cloning vectors (vehicles) useful in the production of protein products.

Masayori Inouye and various of his co-workers have carried out extensive studies involving, gene sequences coding for outer membrane proteins of gram-negative bacteria, in particular, the lipoprotein. These investigations have demonstrated that lipoproteins are present in relatively large quantities in bacterial cells. For example there are approximately $7.2 \times 10^5$ molecules of the lipoprotein of the *Escherichia coli* outer membrane per cell. Moreover, since it appears that there is only one structural gene for the lipoprotein in the *E. coli* chromosome, its transcription machinery must be highly efficient.

Recent efforts of Inouye and associates have been directed to expression of lipoprotein using appropriately formulated plasmids in suitably transformed microorganisms and to determining and analyzing DNA sequences of various lipoprotein genes (lpp). Thus, in Nakamura and Inouye, *Cell* 18, 1109-1117 (1979), the DNA sequence for the outer membrane lipoprotein of *E. coli* is reported. An analysis of the promoter region of this sequence demonstrated some interesting features. First, it was noted that the segment of 261 base pairs (bp) preceding the transcription initiation site ($-1$ to $-261$) has a very high AT content (70%) in contrast to 53% for the 322 bp mRNA region, 44% for the segment of 127 bp after the transcription termination site and and 49% for the average AT content of the *E. coli* chromosome. Secondly, it was noted that the first 45 bp upstream from the transcription initiation site ($-1$ to $-45$) contained 36 bases (80%) which are A or T. Thirdly, a heptanucleotide sequence analogous to the "Pribnow box" is present eight bases from the transcription initiation site. Fourthly, a sequence analogous to the "RNA polymerase recognition site" is present on both strands between positions $-27$ and $-39$. Fifthly, a long dyad symmetry is centered at the transcription initiation site.

It is postulated by Inouye and associates that these features either separately or in combination are responsible for the high degree of lpp promoter strength In particular, it is postulated that the high AT content in the promoter sequence tends to destabilize the helix structure of the DNA and thereby facilitates strand unwinding that is essential for initiation of transcription.

The Inouye group further has shown that a high degree of homology exists with respect to lipoprotein gene sequences of other, perhaps all, gram-negative bacteria. Thus, an analysis of the DNA sequence of the *Serratia marcescens* lipoprotein gene and comparison with that of the *E. coli* lpp gene shows a high degree of homology. [Nakamura and Inouye, *Proc. Natl. Acad. Sci. U.S.A.* 77, 1369-1373 (1980)]. In particular, they showed that the promoter region is highly conserved (84% homology), having an extremely high A and T content (78%) just as in *E. coli* (80%). Moreover, the 5' untranslated region of the lipoprotein mRNA is also highly conserved (95% homology).

More recently, in Yamagata, Nakamura, and Inouye, *J. Biol. Chem.* 256, 2194-2198 (1981), the DNA sequence of the lipoprotein gene of *Erwinia amylovora* was analyzed and compared with those of *E. coli* and *S. marcescens*. This study again confirms the high degree of homology existing in the lpp genes. Thus, the promoter region ($-45$ to $-1$) is highly conserved (87% relative to *E. coli* and 93% to *S. marcescens*). An extremely high A and T content (80%) exists, just as in *E. coli* (80%) and *S. marcescens* (78%). Moreover, the sequence of the untranslated region of the mRNA is highly conserved (97% relative to *E. coli* and 92% to *S. marcescens*).

The high level of constitutive transcription observed for the lipoprotein gene, based upon Inouye's studies, recommends it as a vehicle for expression of exogenous DNA fragments. Moreover, the work of Inouye et al. suggest that any of a wide range of lipoprotein genes of gram-negative bacteria may be so employed, including, for example, *Escherichia coli, Shigella dysenteriae, Salmonella typhimurium, Citrobacter freundii, Klebsiella aerogenes, Enterobacter aerogenes, Edwardsiella tarda, Erwinia amylovora, Serratia marcescens*, and the like.

Most recently, the suitability of the lipoprotein gene for product expression has been demonstrated by Inouye et al. (C. Lee, Nakamura, and Inouye, *J. Bacter.* 146, 861-866 (1981). In this work the *S. marcescens* lipoprotein gene was cloned in a lambda phage vector and then recloned in plasmid vectors pBR322 and pSC101. Both vectors carrying the *S. marcescens* lpp gene were used to transform *E. coli* cells. The evidence establishes normal expression, albeit at a level somewhat reduced relative to vectors containing the *E. coli* lpp gene. In any event, it has been established in the literature that vectors containing the lpp gene promoter and 5' untranslated regions can be employed to achieve significant levels of lipoprotein expression.

By the term "vector" as used herein is meant a plasmid, phage DNA, or other DNA sequence (1) that is able to replicate in a host cell, (2) that is able to transform a host cell, and (3) that contains a marker suitable for use in identifying transformed cells.

It is to a specific class of cloning vectors that this invention is directed. It has been discovered that significantly high levels of expression of exogenous protein can be achieved using cloning vectors constructed to contain, in tandem, a nucleotide sequence defining the lipoprotein promoter region, a nucleotide sequence defining the lipoprotein 5' untranslated region, and a sequence coding for an exogenous protein product, the sequence coding for such product being connected via a translation start signal codon and a nucleotide sequence coding for an enterokinase cleavage site to the 3' terminal of the 5' untranslated region of the lipoprotein gene. Cloning vectors containing such elements therefore represent the subject matter of this invention.

SUMMARY OF THE INVENTION

Thus, this invention is directed to a recombinant DNA cloning vector useful for expressing exogenous protein, which comprises (a) DNA segment containing a functional origin of replication;

(b) one or more DNA segments, each of which conveys to a transformable host cell a property useful for selection when said vector is transformed into said host cell; and (c) a DNA segment comprising a sequence that defines, in tandem,
   (1) the promoter of a lipoprotein expression control sequence,
   (2) the 5' untranslated region of a lipoprotein expression control sequence and
   (3) a translation start codon followed, without interposition of a portion or all of a nucleotide sequence coding for endogenous protein, by a nucleotide sequence coding for an enterokinase cleavage site to which is joined, without interruption, a nucleotide sequence coding for an exogenous protein.

In addition, this invention is directed to certain products available using the recombinant DNA cloning vectors. These products are proteins which carry the sequence Met-Phe-Pro-Leu-Asp-Asp-Asp-Asp-Lys at their amino terminal. Specific such products are Met-Phe-Pro-Leu-Asp-Asp-Asp-Asp-Lys-bovine growth hormone and Met-Phe-Pro-Leu-Asp-Asp-Asp-Asp-Lys-human growth hormone.

DETAILED DESCRIPTION OF THE INVENTION

Figure 1:
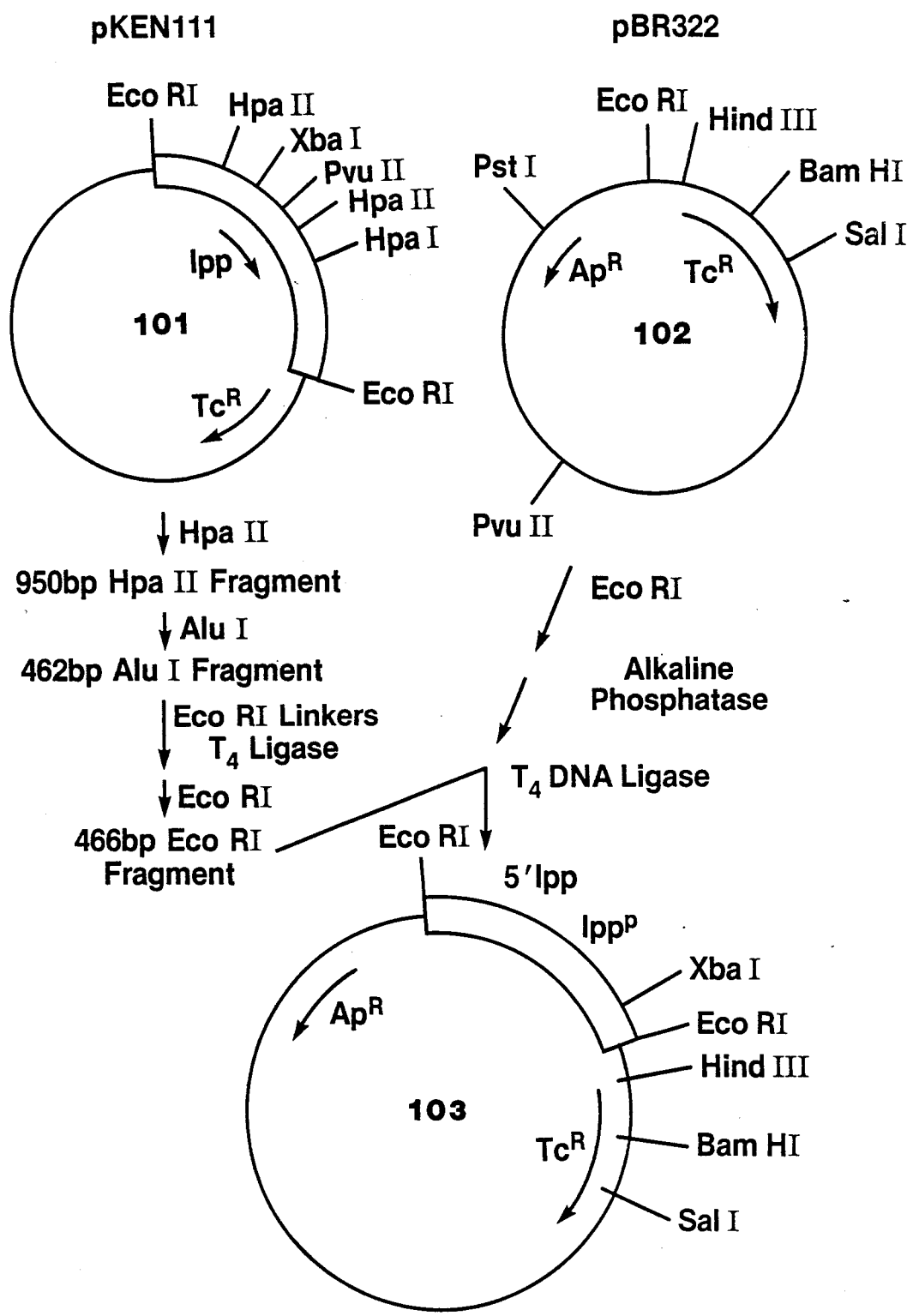

As noted, this invention is directed to DNA sequences and recombinant DNA cloning vectors that are highly efficient in producing exogenous protein. Each of these employs at least a portion of a lipoprotein gene (lpp) machinery, and, preferably, a lipoprotein gene from gram-negative bacteria. By the term "exogenous protein" as used herein is meant a protein product other than the lipoprotein molecule normally expressed by the lipoprotein gene machinery or any portion of such molecule.

Examples of typical gram-negative bacteria which may serve as a source of lpp machinery are, for example, *Escherichia coli, Shigella dysenteriae, Salmonella typhimurium, Citrobacter freundii, Klebsiella Aerogenes, Enterobacter aeroqenes, Edwardsiella tarda, Erwinia amylovora, Serratia marcescens,* and the like.

The lpp gene can be described in terms of five elements. In the order in which they appear in the gene, these elements are as follows: (1) the promoter region; (2) the 5' untranslated region; (3) the lipoprotein coding sequence; (4) the 3' untranslated region; and (5) the transcription termination site.

The function of each of these elements in gene systems is well recognized. The promoter region mediates initiation of messenger RNA (mRNA) production (transcription). The promoter may be free of external control (constitutive), under the control of a repressor, a substance that, when present, represses gene function, or under the control of an inducer, a substance that is required to induce gene function. The lpp gene is free from external control and thus is termed "constitutive".

Located at or near the promoter is the "transcription initiation site", a point at which RNA polymerase binds to initiate transcription of mRNA. Once transcription is initiated, mRNA is produced. The structure of the resulting mRNA is determined by the DNA sequences of the gene elements (2) to (4) above.

The resulting mRNA carries a sequence which is translatable into protein product. The translatable sequence is located downstream of the 5' untranslated region and upstream of the 3' untranslated region. Translation is mediated by binding of ribosomes to a sequence in the mRNA 5' untranslated region denoted as the ribosome binding site and is initiated at the translation start codon (AUG) appearing as the first codon of the product gene sequence and coding as well for the amino acid methionine (Met). Translation terminates at one or more termination codons appearing at the end of the translation region.

By the techniques of recombinant DNA, it has become possible to prepare cloning vectors useful for the production of foreign (exogenous) proteins by inserting into such vectors an expression control sequence, i.e., a sequence of nucleotides that controls and regulates expression of structural genes when operatively linked to those genes. In the subject matter of this invention, the cloning vectors involve use of a portion or all of the lpp expression control sequence, which includes elements (1), (2), (4), and (5) as aforedescribed. Of these four elements, in the cloning vectors of this invention, only elements (1) and (2), the promoter region and the 5' untranslated region are required.

It has been customary, using recombinant DNA methodology, to produce a foreign protein by inserting a DNA sequence coding for such foreign protein into the expression control sequence of a cloning vector at a point such that the product expressed comprises a hybrid protein. By "hybrid protein" as used herein is meant a recombinant DNA product comprising all or a portion of the natural (endogenous) protein produced by the expression control sequence (in this case, lipoprotein) to which is attached the foreign (exogenous) protein.

The properly designed hybrid protein will contain a cleavage site at the junction of the endogenous protein portion and the exogenous protein. The cleavage site permits generation of mature exogenous protein product by chemical or enzymatic treatment of the hybrid protein product.

As noted hereinbefore, it has been determined that the lpp expression control sequence is useful for expression of exogenous proteins. Most recently, however, it has been discovered that the lpp expression control sequence can be used to great advantage to express exogenous protein when the construction is designed such that the DNA sequence coding for exogenous protein is joined to a translation start codon through a sequence coding for an enterokinase cleavage site in contradistinction to a hybrid protein comprising lipoprotein or a portion thereof and exogenous protein.

In constructing the cloning vectors of this invention, several elements are required. Two of the required elements are common to all useful cloning vectors. First, the vector must have a DNA segment containing a functional origin of replication (replicon). Plasmids and phage DNA by their very nature contain replicons facilitating replication in a host cell.

Secondly, the vector must have a DNA segment which conveys to a transformable host cell a property useful for selection of transformed cells from nontransformed cells. Any of a wide range of properties can be used for selection purposes. One of the most commonly used properties is antibiotic resistance, e.g., tetracycline resistance or ampicillin resistance.

The foregoing two elements generally are present in readily available and recognized cloning vectors. Examples of suitable cloning vectors are bacterial plasmids, such as plasmids from *E. coli*, including pBR322, pMB89, ColEl, pCRl; wider host range plasmids, including RP4; phage DNAs, such as lambda, and the like. Most, if not all, of the above-recognized vectors already carry the aforedescribed two elements.

A third element, specific to the vectors of this invention, is the lipoprotein expression control sequence. The *E. coli* lipoprotein expression control sequence, present in plasmid pKEN111 and cultured in *E. coli* CC620, has been deposited and made a part of the stock culture collection of the Northern Regional Research Center, Agricultural Research, North Central Region, 1815 North University Street, Peoria, Ill., 61604, from which it is available to the public under the accession number NRRL 15011. The lipoprotein expression control sequence can be removed from pKEN111 using recognized restriction sites and their corresponding restriction endonucleases. Any of a wide range of other lipoprotein expression control sequences also are available using recognized methodology. Such methods may involve, for example, preparation by synthesis or by isolation of a probe using available 1pp sequences (e.g. pKEN111), and, taking advantage of the high degree of homology which exists between 1pp sequences, using such probe for selecting, by hybridization, 1pp sequences from other sources.

In producing a suitable cloning vector by insertion of the lipoprotein expression control sequence, routine methods also are used. Various sites exist within cloning vectors at which cuts can be made using a restriction endonuclease specific for such site. Any of these sites can be selected for insertion of the lipoprotein expression control sequence. As an example, in the well-recognized and documented plasmid pBR322, several suitable restriction sites exist, any of which may be employed as insertion sites. A PstI site is located within the gene for β-lactamase. Other sites outside of any specific coding region are EcoRI and PvuII. These and other sites are well recognized by those skilled in the art.

Taking advantage of any of these sites or others, insertion of a lipoprotein expression control sequence or the essential portion thereof can be readily accomplished in production of vectors defined by this invention.

A fourth element, again specific to the vectors of this invention, is the DNA sequence coding for the exogenous protein. The key requirement with respect to the exogenous protein DNA sequence in the vectors of this invention concerns its location. It must be located downstream of the 3' end of the 5' untranslated region of the lipoprotein expression control sequence and in connection therewith via a translation start codon followed by a nucleotide sequence which codes for an enterokinase cleavage site. Necessarily, in the vectors of this invention, none of the DNA sequence coding for lipoprotein may be interposed between the 5' untranslated region and the sequence coding for exogenous protein.

A fifth element, also specific to the vectors of this invention, is the aforementioned nucleotide sequence coding for an amino acid sequence recognized and cleaved at its carboxyl terminal by the enzyme enterokinase. The nucleotide sequence coding for an enterokinase-cleavable amino acid sequence is joined at its 5' end to the translation start codon and at its 3' end to the 5' end of the nucleotide sequence coding for the exogenous protein and is designed such that the resulting translation product comprising (methionine)-(enterokinase cleavage site)-(exogenous protein) can, by treatment with enterokinase, be cleaved with production of mature exogenous protein.

Enterokinase (3.4.21.9) has been described as "one of many hydrolases located in the brush border membrane of the intestinal duodenum." (J. J. Liepnieks and A. Light, *J. Biol. Chem.* 254, 1677–1683 (1979)). Its isolation and purification have been described in numerous publications, see, for example, Liepnieks, supra; S. Maroux, J. Baratti, and P. Desnuelle, *J. Biol. Chem.* 246, 5031–5039 (1971), and J. Baratti, S. Maroux, D. Louvard, and P. Desnuelle, *Biochimica et Biophysica Acta* 315, 147–161 (1973).

Enterokinase appears to cleave a peptide at the carboxyl of a lysine (Lys) residue that is preceded by a multiplicity of acidic amino acids, i.e., glutamic acid (Glu) and/or aspartic acid (Asp). Thus, in A. Light, H. S. Savithri, and J. J. Liepnieks, *Anal. Biochem.* 106, 199–206 (1980), a number of amino acid sequences recognized by enterokinase are described, including many of the following:

Phe-Pro-Leu-Asp-Asp-Asp-Asp-Lys;
Val-Asp-Asp-Asp-Asp-Lys;
Phe-Pro-Ile-Glu-Glu-Asp-Lys;
Leu-Pro-Leu-Glu-Asp-Asp-Lys;
Ala-Asp-Asp-Lys;
Asp-Asp-Asp-Asp-Lys;
and the like.

The nucleotide sequences coding for any of the above as well as others can be present in the cloning vectors of this invention. The only requirement is that the nucleotide sequence be one which codes for an amino acid sequence that is recognized by and, when present in a longer chain peptide, cleaved at its carboxyl terminal by enterokinase.

In construction of vectors meeting these requirements, advantage can be made of a unique XbaI restriction site that appears in the 5' untranslated region of the *E. coli* lipoprotein expression control sequence. A cut can be made at the XbaI site with removal of a portion of the 5' untranslated region. Using recognized oligonucleotide synthesis methodology, a linker can be prepared comprising the removed portion of the 5' untranslated region to which is coupled a DNA sequence coding for a start codon, the enterokinase cleavage site, and a portion or all of the exogenous protein.

The DNA sequence coding for exogenous protein can be constructed synthetically, e.g., using the recognized phosphotriester method or other well-recognized methods, or its DNA sequence can be obtained by recognized methodology as a copy from isolated mRNA. Once so obtained, the cDNA copy can be cut at a restriction site located at a point as near the start codon as is available. A linker composed of the lipoprotein 5' untranslated region fragment removed by the XbaI cleavage followed by start codon, enterokinase cleavage site, and the cleaved portion of the exogenous protein, can thus be prepared synthetically. This linker, sufficient to bridge the gap, then is used in conjunction with remaining available elements of the lipoprotein expression control sequence to prepare a vector as defined by this invention.

The cloning vectors of this invention can be used to produce any of a wide range of exogenous proteins, including mammalian and human hormones, enzymes, and immunogenic proteins (or intermediates therefor). Examples of such products are insulin A chain, insulin B chain, proinsulin, interferon, growth hormone, antigenic proteins for foot and mouth disease, somatostatin, β-endorphin, and the like. Preferred cloning vectors are those designed for the production of human growth hormone or bovine growth hormone. It will be recognized that the expression product will comprise methionine (start codon), enterokinase cleavage site, and exogenous protein. Mature exogenous protein is generated by treating the expression product with enterokinase in accordance with recognized methodology (see, for example, Light et al., supra).

The cloning vectors of this invention can be used in a wide range of host organisms, for example, gram-negative prokaryotic organisms such as *Escherichia coli, Serratia, Pseudomonas,* and the like; gram-positive prokaryotic organisms, such as Bacillus, Streptomyces, and the like; and eukaryotic organisms, such as Saccharomyces, and the like. Preferably, the host organism is a gram-negative prokaryotic organism. Of gram-negative prokaryotic organisms, *E. coli* is especially preferred, for example, *E. coli* K-12 strains, such as RV308.

Employing well recognized methodology, the cloning vectors of this invention are used to transform suitable host organisms, are amplified in such organisms, and exogenous protein product is expressed using standard fermentation conditions. The exogenous protein product is isolated by routine methods from the resulting fermentation broth.

The structure and function of cloning vectors of this invention is illustrated by the examples which follow, which examples are to be read and understood in conjunction with the accompanying drawings in which:

FIGS. 1-5 together comprise a schematic illustration of a method as described in Example 1 following for constructing a cloning vector of this invention useful for the production of human growth hormone.

Figure 6:
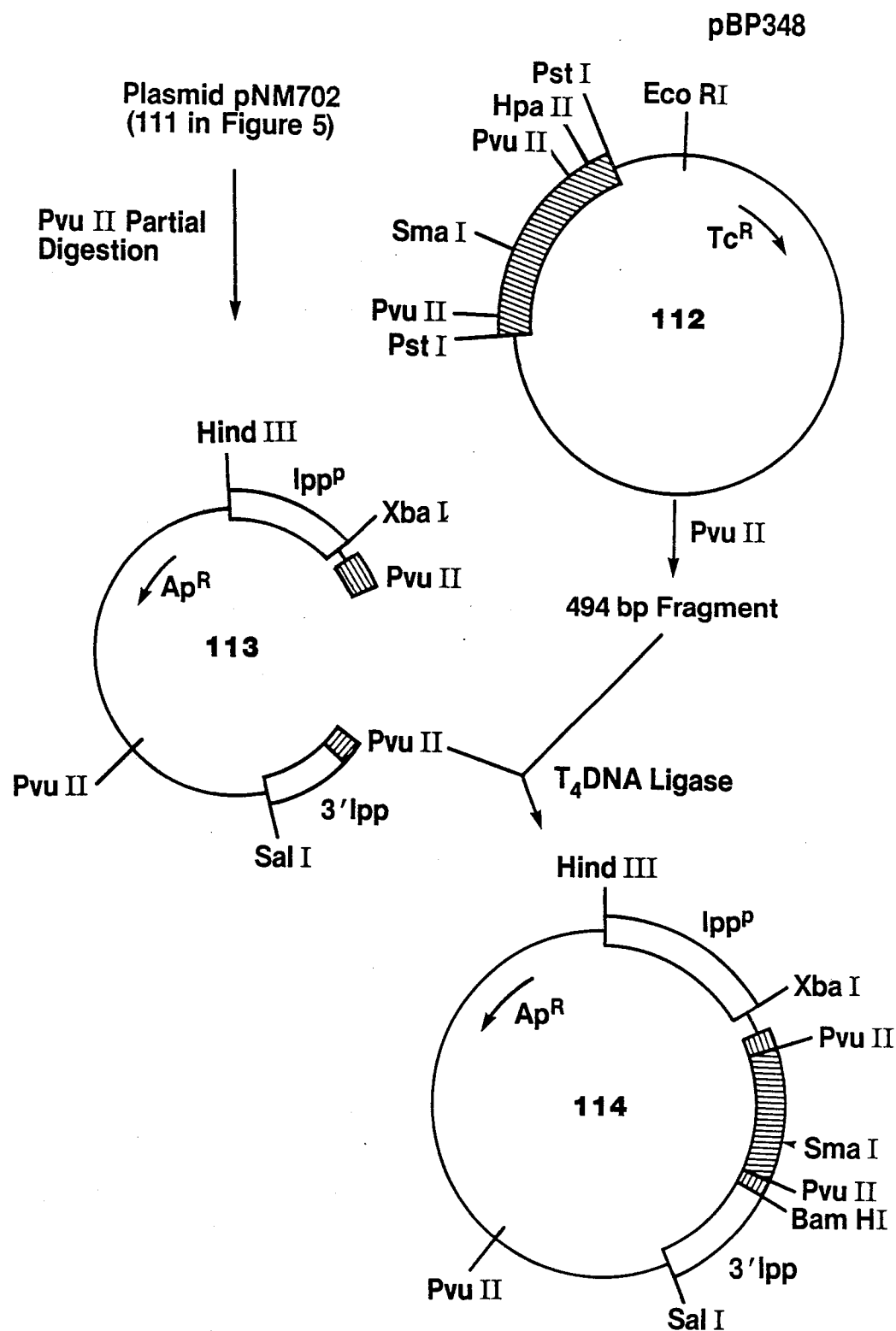
Figure 7:
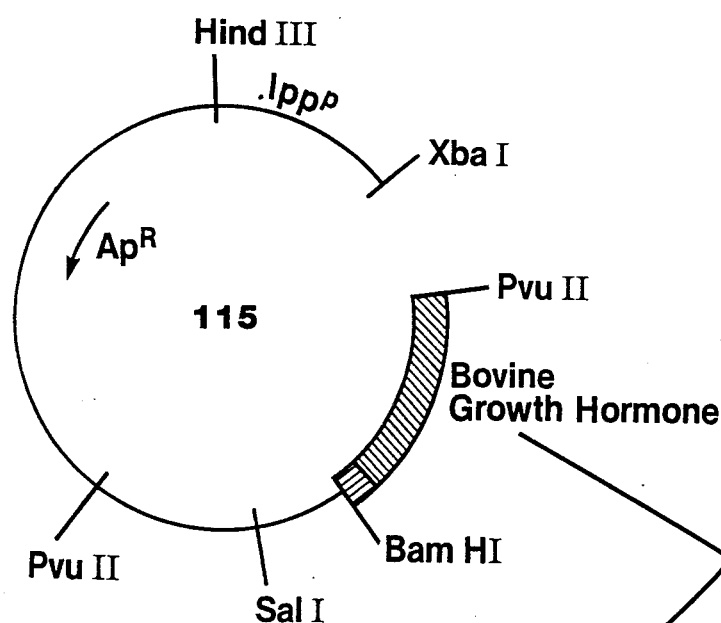
Figure 7:
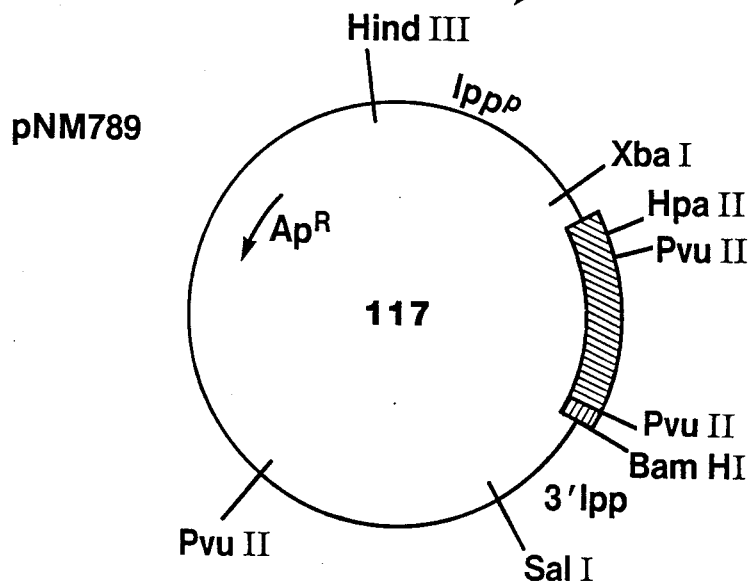
Figure 8:
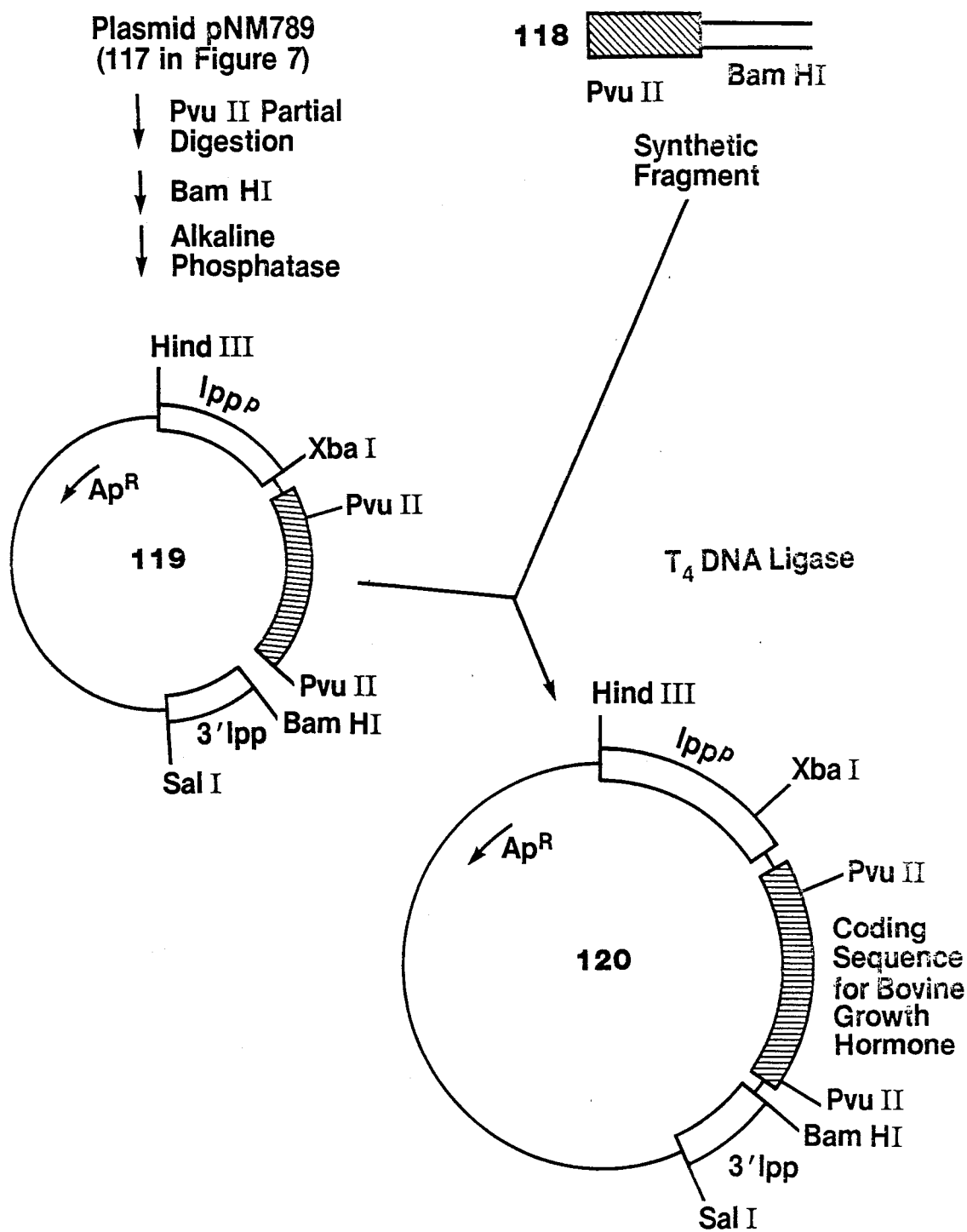

FIGS. 6-8 together and in conjunction with FIGS. 1-5 comprise a schematic illustration of a method as described in Example 2 following for constructing a cloning vector of this invention useful for the production of bovine growth hormone.

Figure 9:
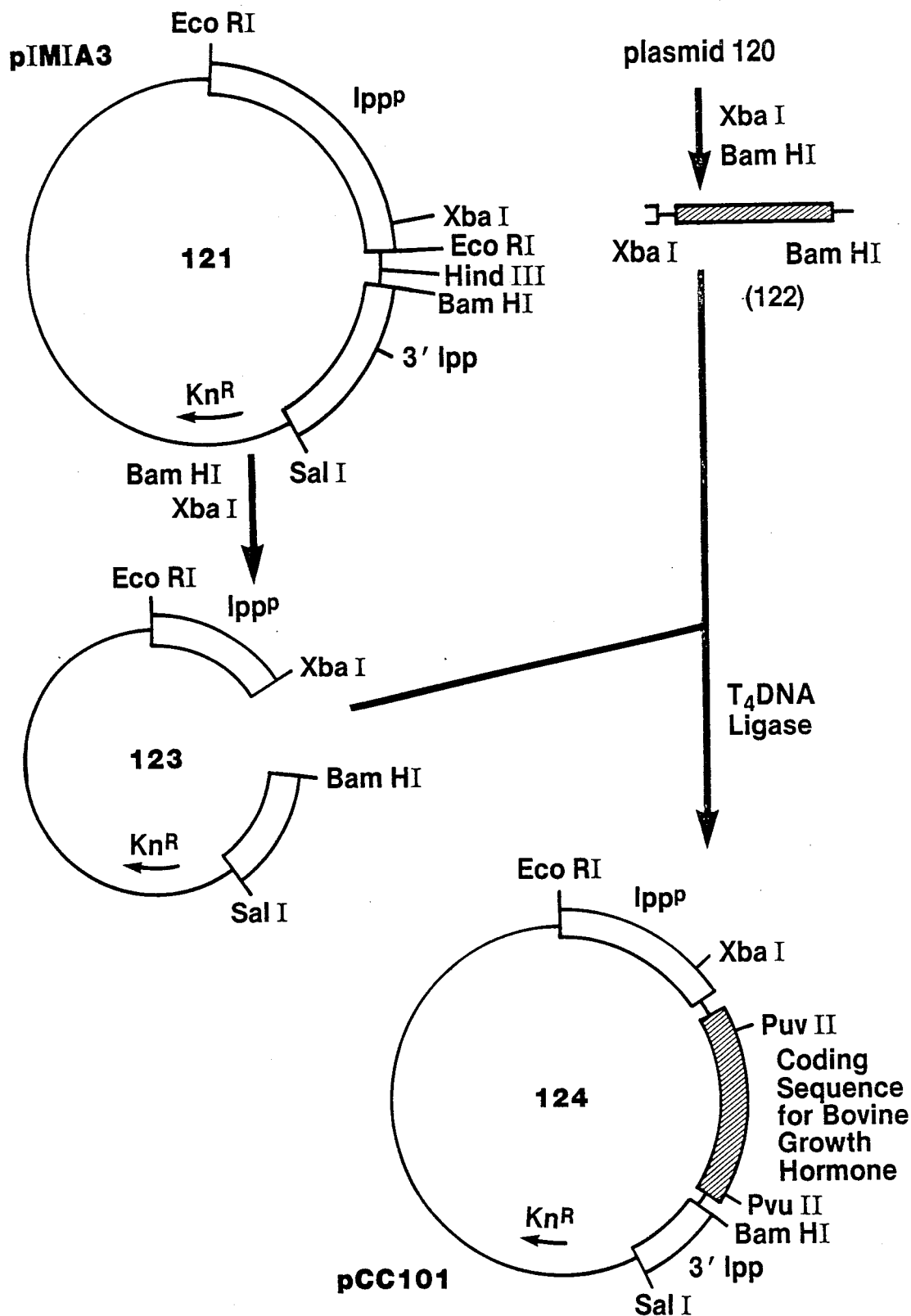

FIG. 9 shows the construction of pCC101.

EXAMPLE 1

Plasmid for the Expression of
Met-Phe-Pro-Leu-Asp-Asp-Asp-Asp-Lys-Human
Growth Hormone and Its Use as Substrate for Selective
Cleavage by Enterokinase (3.4.21.9) to Produce Mature
Human Growth Hormone The ~5.1kb (kilobase) fragment produced by XbaI (5'TCTAGA3'), BamHI (5'GGATCC3') cleavage of plasmid vector pKEN021 (106 in FIG. 3) was used as starting material. pKEN021 is a derivative of pKEN111 (101 in FIG. 1) (Lee, N., et al., *J. Bact.* 146, 861–866 (1981) and Zwiebel, L. J., et al., *J. Bact.* 145, 654–656 (1981), which is on deposit in *E. coli* CC620 at the Northern Regional Research Center (NRRL), Agricultural Research Service, U.S. Department of Agriculture, Peoria, Ill. 61604, receiving the Accession No. NRRL B-15011. Plasmid pKEN111 has a 2.8 kb fragment which contains the lipoprotein gene of *E. coli.* A description of this fragment is provided in Nakamura, K. and Inouye, M., *Cell* 18, 1109–1117 (1979). In pKEN021 the 650 bp (base pair) sequence between the unique EcoRI (5'GAATTC3') and SalI (5'GTCGAC3') restriction sites of pBR322 has been replaced by sequences taken from the lipoprotein gene of *E. coli.* The nucleotide sequence of all functional parts of this gene has been determined. The lipoprotein gene sequence (Nakamura, K. and Inouye, M., *Cell* 18, 1109–1117 (1979)) includes a 462 bp AluI (5'AGCT3') fragment upstream of the first codon (methionine) of the lipoprotein gene. This fragment contains the promoter, the 5' untranslated region and the ribosome binding site. A unique XbaI (5'TCTAGA3') restriction site is located within the ribosome binding site 16 bp before the translation initiating methionine codon. A PvuII (5'CAGCTG3') restriction site located 105 bp upstream of the translation termination codon of the structural gene was changed to a BamHI (5'GGATCC3') restriction site by the addition of a synthetic DNA adapter fragment, (5'CCGGATCCGG3', obtained from Collaborative Research). The coding sequence for the last thirty-five amino acids of lipoprotein, the translation termination codon, and the sequence corresponding to the 3' untranslated region of the messenger RNA follow the BamHI site. Plasmid pKEN021 also includes some 850 bp of extraneous sequences unrelated to the lipoprotein gene and located downstream of it in the *E. coli* chromosome. These sequences were included as a consequence of the methods and restriction enzyme sites used in the original isolation of the gene.

Figure 2:
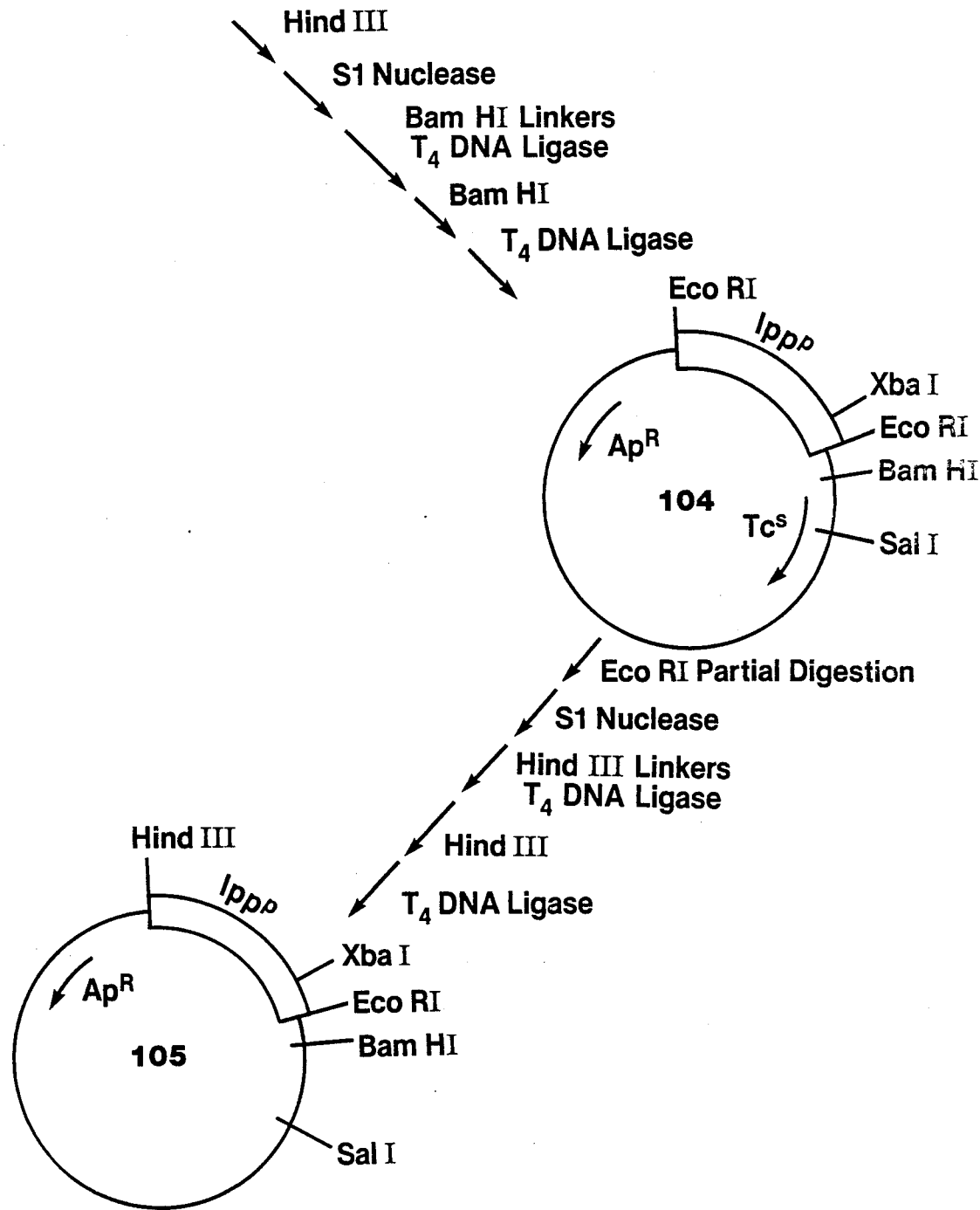
Figure 3:
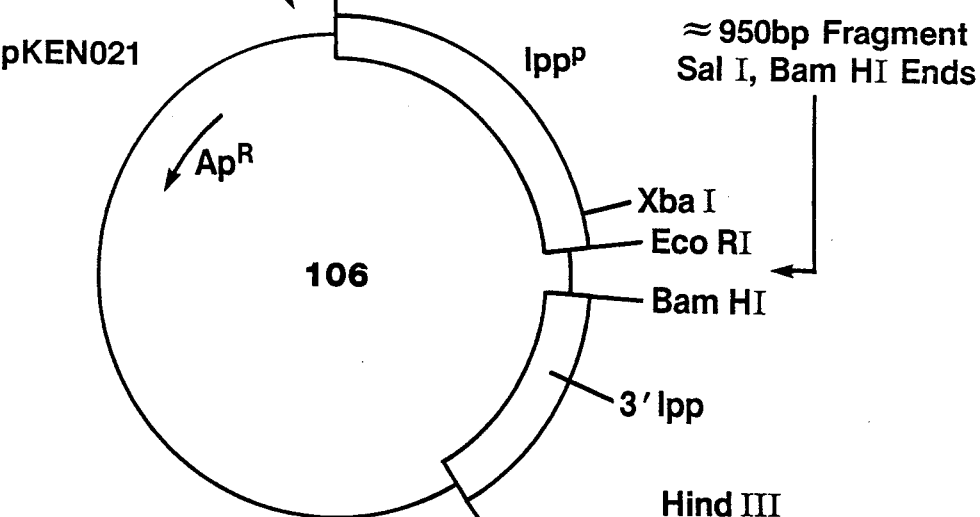
Figure 3:
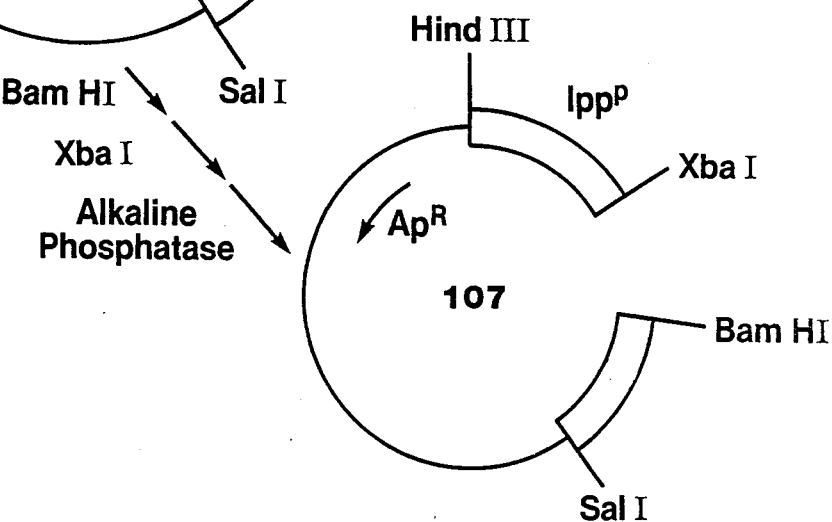
Figure 4:
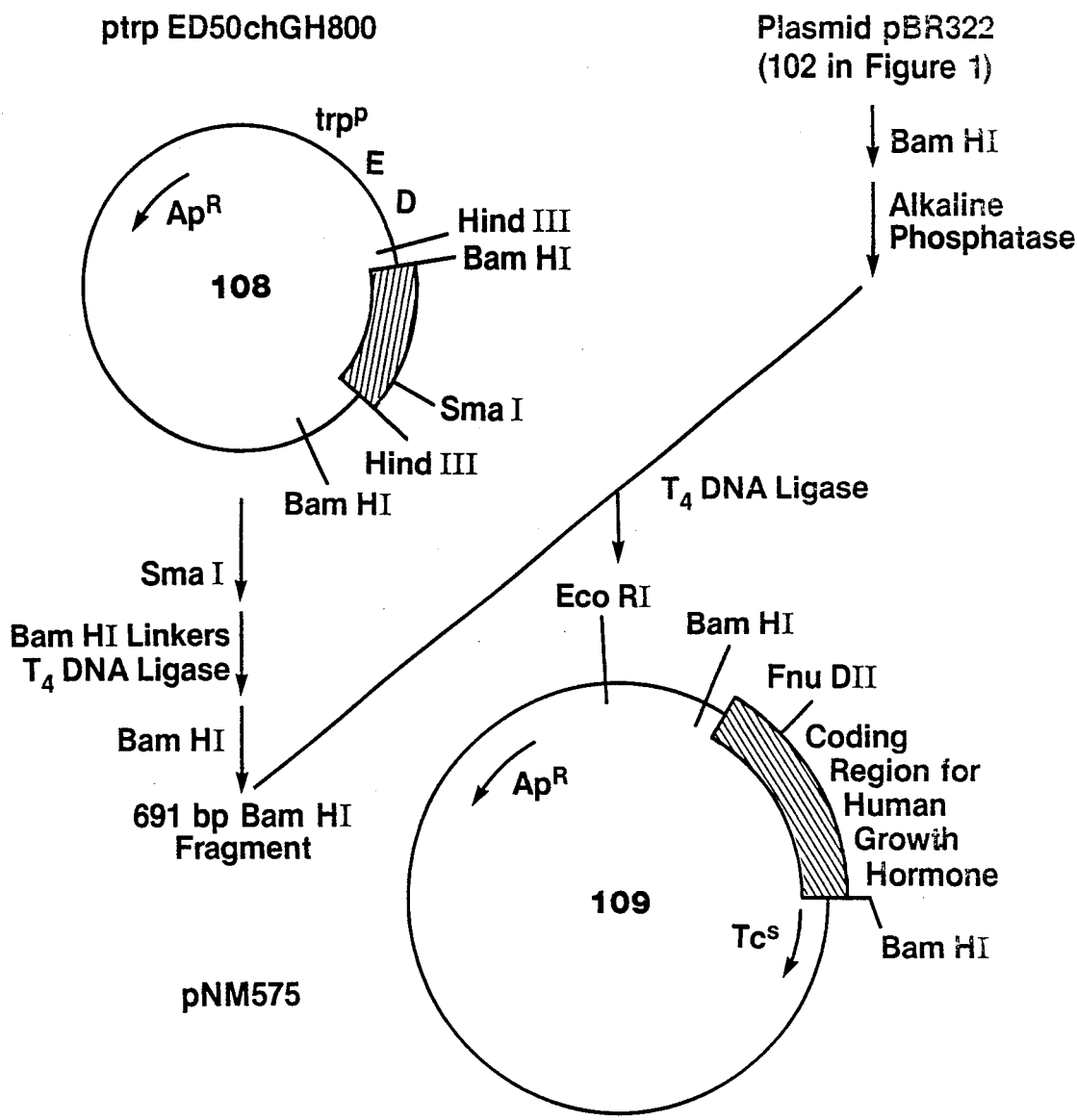
Figure 5:
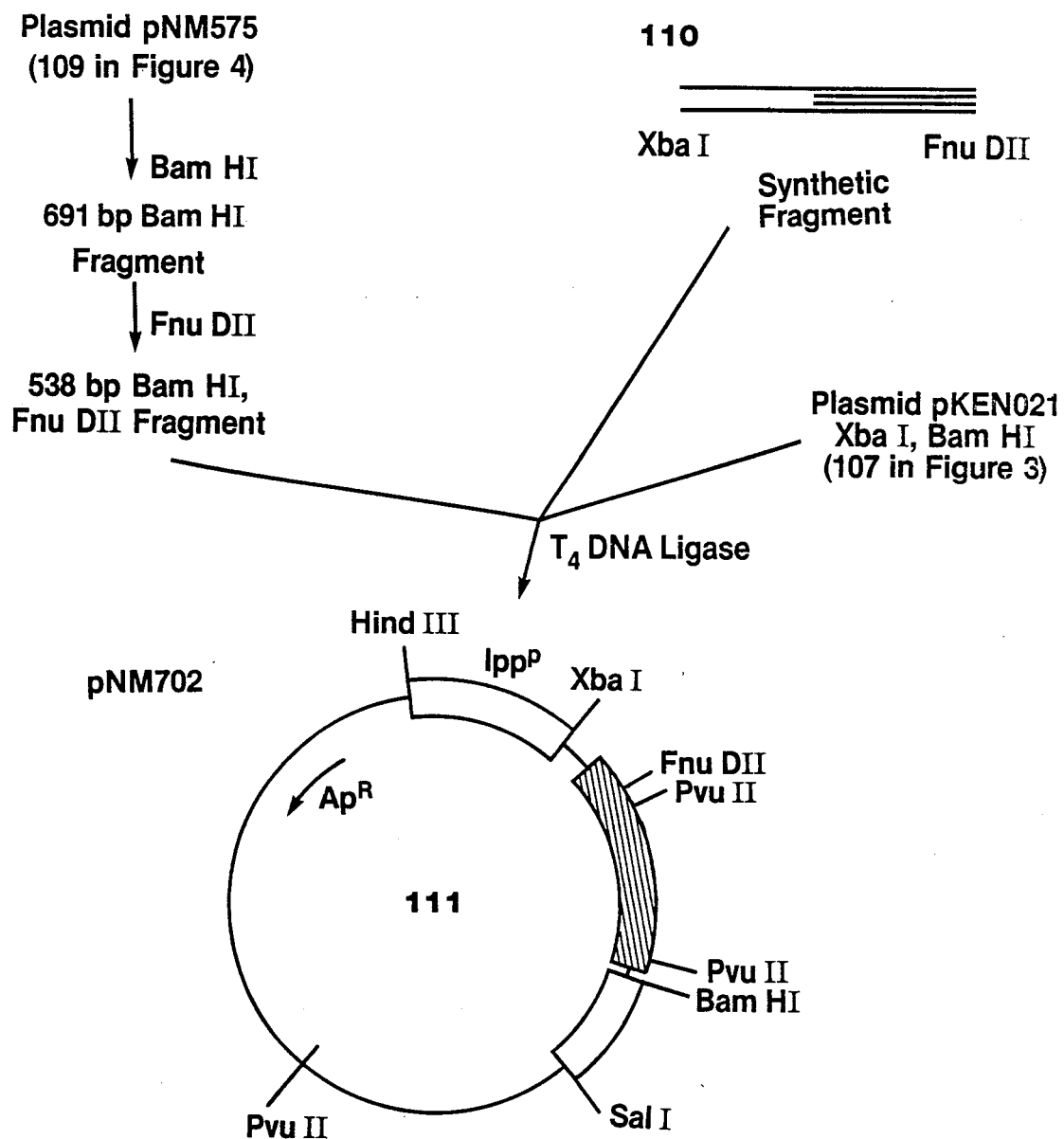

Referring to FIGS. 1, 2, and 3, plasmid pKEN021 is derived from pKEN111 in the following manner: Fifty micrograms of pKEN111 (101 in FIG. 1) are digested with 25 units of restriction enzyme HpaII (5'CCGG3') in 300 μl of a buffer containing 20 mM Tris:HCl pH 7.4, 10 mM MgCl$_2$, and 6 mM β-mercaptoethanol at 37° C. for 2 hours. The mixture is extracted twice with 300 μl of a 50:50 mixture of phenol and chloroform, and the recovered aqueous phase is precipitated with 2.5 volumes of ethanol. The DNA pellet is dissolved in 100 μl of electrophoresis buffer and fractionated on a 5 percent polyacrylamide gel (acrylamide:bis ratio is 29:1 in all gels except where noted). The gel is stained in a solution containing 0.5 μg/ml of ethidium bromide and bands are visualized under long wave-length ultraviolet light. A 950 bp band is isolated and recovered from the gel by electroelution into a dialysis bag. After phenol/CHCl$_3$ extraction and ethanol precipitation the recovered DNA (approximately 2.5 μg) is dissolved in 25 μl of TEN (10 mM NaCl, 10 mM Tris:HCl pH 7.4 and 1 mM sodium ethylenedinitrilotetraacetate (EDTA) pH 8.0).

Two micrograms of the 950 bp HpaII fragment are digested with restriction enzyme AluI (5'AGCT3') in 200 μl of a buffer containing 50 mM NaCl, 6 mM Tris:HCl (pH 7.6), 6 mM MgCl$_2$, and 6 mM β-mercaptoethanol for 2 hours at 37° C. The DNA is fractionated on a 6 percent polyacrylamide gel, and the 462 bp AluI fragment generated is recovered and purified by the method hereinbefore described. The 462 bp AluI fragment (approximately 1 μg) is dissolved in 10 μl of T$_4$ DNA ligase buffer (66 mM Tris:HCl pH 7.6, 10 mM MgCl$_2$, 10 mM dithiothreitol, 0.4 mM ATP) containing 150 picomoles of phosphorylated EcoRI linker (5'GGAATTCC3' from Collaborative Research) and 2 units T$_4$ DNA ligase. After incubation at 4° C. for 16 hours the mixture is heated at 65° C. for 10 minutes and diluted to 100 μl with the addition of EcoRI buffer (100 mM Tris:HCl pH 7.2, 50 mM NaCl, 10 mM MgCl$_2$, 6 mM β-mercaptoethanol) and 40 units EcoRI enzyme. After 2 hours at 37° C. the sample is phenol/CHCl$_3$ extracted and ethanol precipitated by the method hereinbefore described. The DNA is dissolved in 20 μl of T$_4$ DNA ligase buffer containing 0.1 unit T$_4$ DNA ligase and 0.1 μg pBR322 (102 in FIG. 1) which has been linearized with EcoRI and alkaline phosphatase treated to remove end phosphates. After ligation at 4° C. for 16 hours the material is used to transform a suitable *E. coli* strain (hsr⁻, hsm⁺) such as HB101. The bacterial cells are made competent for transformation using a standard CaCl₂ treatment. Transformants are selected on agar plates containing 12 μg/ml of tetracycline. Plasmids are isolated from several tetracycline resistant colonies by the rapid alkaline extraction procedure described in Birnboim, H. C. and Doly, J., *Nucleic Acids Research* 7, 1513–1523 (1979). A plasmid (103 in FIG. 1) containing a 466 bp XbaI, BamHI fragment (desired orientation) is selected and used as the starting material for the next step.

Two micrograms of this plasmid (103 in FIG. 2) (having one HindIII (5'AAGCTT3') restriction site) are digested with 2 units of HindIII enzyme in 50 μl HindIII buffer (60 mM NaCl, 10 mM Tris:HCl pH 7.4, 10 mM MgCl₂ and 6 mM β-mercaptoethanol) for 1 hour at 37° C. After phenol/CHCl₃ extraction and ethanol precipitation the DNA is dissolved in 200 μl of a buffer containing 300 mM NaCl, 30 mM sodium acetate pH 4.25, 1 mM ZnCl₂ and 200 units of S1 nuclease (Miles Laboratories) which is specific for single stranded DNA. After 1 hour at 15° C. the reaction is stopped by phenol/CHCl₃ extraction and ethanol precipitation. The plasmid, which has now had the single stranded, HindIII-generated ends removed, is dissolved in 10 μl T₄ DNA ligase buffer containing 20 picomoles phosphorylated BamHI linkers (5'CCGGATCCGG3', from Collaborative Research) and 2 units T₄ DNA ligase. After 16 hours at 4° C. the reaction mixture is heated at 65° C. for 10 minutes to inactivate the ligase. The mixture is diluted to 100 μl in BamHI buffer (150 mM NaCl, 20 mM Tris:HCl pH 8.0, 10 mM MgCl₂, 6 mM β-mercaptoethanol) containing 20 units BamHI enzyme. After 2 hours at 37° C. the mixture is purified on a 1 percent agarose gel. The gel is stained and the larger fragment (4.5 kb) is recovered by elution after freezing and purified by phenol/CHCl₃ extraction and ethanol precipitation. The recovered plasmid with BamHI cohesive ends is dissolved in 20 μl of T₄ DNA ligase buffer containing 0.1 unit T₄ DNA ligase. After 16 hours at 4° C. the DNA is used to transform *E. coli* HB101. Transformants are selected by resistance to ampicillin (Ap$^r$) at 100 μg/ml and screened for sensitivity to 10 μg/ml tetracycline (Tc$^s$). Several plasmids are prepared by the previously described Birnboim procedure from colonies which are Ap$^r$Tc$^s$. These are examined for the absence of a HindIII site and the presence of a single BamHI site. EcoRI, SalI sequential digestion yields a 466 bp and a 305 bp fragment. A plasmid (104 in FIG. 2) with these characteristics is selected and is modified to remove the EcoRI site located upstream of the lpp promoter and to convert it to a HindIII restriction site.

Two micrograms of plasmid (104 in FIG. 2) are digested in 100 μl of EcoRI buffer with 0.2 units of EcoRI for 10 minutes at 37° C. The reaction is stopped by heating for 10 minutes at 65° C. After phenol/CHCl₃ extraction the DNA is ethanol precipitated and dissolved in 200 μl of S1 nuclease buffer containing S1 nuclease at 1000 units/ml. After 1 hour at 12° C. the reaction is stopped by phenol/CHCl₃ extraction and ethanol precipitation. The DNA is resuspended in 10 μl of T₄ DNA ligase buffer containing 20 picomoles phosphorylated HindIII linker (5'CCAAGCTTGG3', from Collaborative Research) and 2 units of T₄ DNA ligase. After 16 hours at 4° C. the ligase is inactivated by heating 10 minutes at 65° C. The reaction mixture is diluted to 150 μl in HindIII buffer containing 10 units HindIII enzyme. After incubation for 2 hours at 37° C., the mixture is fractionated on a 1 percent agarose gel. After staining in ethidium bromide, the largest band (equivalent to single cut plasmid) is recovered and purified. The plasmid is dissolved in 20 [21 1 T₄ ligase buffer containing 0.2 units T₄ ligase, incubated 16 hours at 4° C. and used to transform *E. coli* HB101. Transformants are selected for ampicillin resistance and are screened by the Birnboim procedure. Plasmid isolates are analyzed by restriction with EcoRI (1 site) and HindIII (1 site) enzymes. A plasmid (105 in FIG. 2) with an EcoRI, HindIII fragment of 500 bp is selected and used as the cloning vector for addition of the 3' region of the lpp gene.

Two micrograms of plasmid (105 in FIG. 3) are digested in 50 μl of SalI restriction buffer (150 mM NaCl, 6 mM Tris:HCl pH 7.9, 6 mM MgCl₁₂, 6 mM β-mercaptoethanol) with 2 units of SalI for 1 hour at 37° C. The reaction is diluted to 150 μl in BamHI buffer containing 2 units BamHI. After 1 hour at 37° C., 2.5 units of alkaline phosphatase are added and incubation continued for 1 hour at 65° C. The material is phenol/CHCl₃ extracted, ethanol precipitated, dissolved in TEN, and used as cloning vector for the lpp 3' fragment.

To obtain the fragment containing the lpp 3' region, 10 μg of pKEN111 (101 in FIG. 3) are digested in 200 μl of HpaI buffer (20 mM KCl, 10 mM Tris:HCl pH 7.4, 10 mM MgCl₂ and 6 mM β-mercaptoethanol) with 10 units of HpaI (5'GTTAAC3') for 2 hours at 37° C. After phenol/CHCl₃ extraction and ethanol precipitation, the DNA is dissolved in 10 μl T₄ DNA ligase buffer containing 20 picomoles phosphorylated SalI linker (5'GGTCGACC3', from Collaborative Research) and 2 units T₄ DNA ligase. After 16 hours at 4° C. the ligase is inactivated by heating at 65° C. for 10 minutes. The material is diluted to 100 μl in SalI buffer containing 10 units of SalI and incubated 1 hour at 37° C. The DNA is diluted to 300 μl in PvuII buffer (60 mM NaCl, 6 mM Tris:HCl, pH 7.5, 6 mM MgCl₂, 6 mM β-mercaptoethanol) containing 10 units PvuII restriction enzyme. After 1 hour at 37° C. the DNA is fractionated on a 5 percent polyacrylamide gel. Approximately 0.5 μg of a 950 bp fragment is recovered, purified and dissolved in TEN. Two-tenths microgram of fragment is diluted into 20 μl T₄ DNA ligase buffer containing 20 picomoles phosphorylated BamHI linker (5'CCGGATCCGG3', from Collaborative Research) and 2 units T₄ DNA ligase. After 16 hours at 4° C. the ligase is inactivated by heating 10 minutes at 65° C. The DNA is diluted to 100 μl in BamHI buffer containing 20 units BamHI. After 2 hours at 37° C. the DNA is fractionated on a 5 percent polyacrylamide gel to remove excess linker molecules. The 950 bp fragment having BamHI and SalI cohesive ends is recovered and purified. The fragment is dissolved in 20 μl of T₄ DNA ligase buffer containing 0.2 μg of cloning vector described previously and 0.2 units T₄ DNA ligase. After incubation for 16 hours at 4° C. the material is used to transform *E. coli* HB101. Plasmids are prepared from ampicillin resistant transformants and analyzed for a SalI, BamHI fragment of 950 bp. The desired plasmid (5.2 kb) is designated pKEN021 (106 in FIG. 3).

Ten micrograms of pKEN021 were digested in 200 μl of XbaI/BamHI buffer (150 mM NaCl, 10 mM Tris:HCl pH 8, 10 mM MgCl₂, 6 mM β-mercaptoethanol) using 10 units of BamHI for 1 hour at 37° C. followed by 10 units of XbaI for 1 hour at 37° C. The DNA was then treated with 2.5 units of alkaline phosphatase for 1.5 hours at 65° C., phenol/CHCl₃ extracted, collected by ethanol precipitation, and dissolved in 50 μl of TEN (10 mM Tris:HCl pH 7.4, 10 mM NaCl, 1 mM EDTA) for 0.2 μg/μl. This preparation (107 in FIG. 3) was used as the plasmid cloning vector.

Plasmid ptrpED50chGH800 (108 in FIG. 4), described in Martial, J. H., et al., *Science* 205, 602-607 (1979), was used as the source of a DNA fragment containing the coding sequence for a portion of the human growth hormone gene. This fragment also is available using recognized methodology for isolating mRNA coding for human growth hormone from human pituitaries. Such methodology is described by Goodman, H. M., et al., *Methods in Enzymology* 68, 75-90 (1979). The human growth hormone gene portion of plasmid ptrpED50chGH800 contains a unique SmaI (5'CCCGGG3') restriction site 6 bp downstream from the translation termination codon of the gene. This site was changed to a BamHI site using the following procedure: 6 μg of the plasmid were digested with 6 units of SmaI in 200 μl of SmaI restriction buffer (15mM Tris:HCl pH 8.0, 6 mM MgCl$_2$, 15 mM KCl and 6 mM β-mercaptoethanol) for 1.5 hours at 37° C. After digestion was complete, phenol/CHCl$_3$ extraction was performed, and the DNA was recovered by ethanol precipitation. The precipitated DNA was dissolved in 24 μl of TEN. Forty picomoles of phosphorylated BamHI adapter fragment (Collaborative Research) were added to 0.5 μg (0.2 picomole ends) of the above digested plasmid in 16 μl of ligase buffer containing 2 units T$_4$ DNA ligase. Ligation was allowed to occur 2 hours at 22° C. and 16 hours at 4° C. T$_4$ DNA ligase was inactivated at 65° C. for 10 minutes. BamHI cohesive termini were generated by dilution into BamHI buffer containing 20 units BamHI enzyme in a final total volume of 40 μl followed by incubation at 37° C. for 1 hour. The enzyme cleaved the linker sequence as well as a BamHI site located at the beginning of the cloned cDNA sequence of human growth hormone. This yielded a 691 bp fragment with cohesive BamHI ends which was separated on a 6 percent polyacrylamide gel and visualized under long wavelength ultraviolet light after staining in an ethidium bromide solution at 1 μg/ml. The gel region containing the fragment was excised and the DNA fragment was recovered by electroelution into a dialysis bag followed by ethanol precipitation. The precipitated DNA was recovered by centrifugation, dissolved in TEN, phenol/CHCl$_3$ extracted to remove ethidium bromide and ethanol precipitated. The recovered DNA fragment was ligated (using 0.2 unit T$_4$ DNA ligase in 20 μl of buffer under previously described conditions) with 0.2 μg pBR322 (102 in FIG. 4) which had been cleaved at its unique BamHI site and treated with alkaline phosphatase. After 16 hours at 4° C. the material was used to transform *E. coli* strain JA221 (recA$^-$, hrs$^-$hsm$^+$, Δtop F 5, thr, leu, thi, lacY$^-$) which is on deposit as NRRL Deposit No. 15014. A transformation procedure as described by Wensink, P. C. et al., *Cell* 3, 315-325 (1974) was used, and transformed colonies were selected on agar plates containing 100 μg/ml ampicillin. Plasmid DNAs were isolated from sixteen of the ampicillin resistant colonies by the rapid alkaline-denaturation method previously described by Birnboim and then analyzed by restriction enzyme digestion and gel electrophoresis. Eleven of the sixteen plasmids examined were found to contain a BamHI fragment of approximately 700 bp. One of these plasmids pNM575 (109 in FIG. 4) was chosen for amplification to use as a source of DNA fragment for the plasmid construction to be described. The DNA sequence of mature human growth hormone contains one FnuDII (5'CGCG3') site which is 47 bp from the first nucleotide. There are 23 recognition sites for this enzyme in pBR322. Twenty-five micrograms of pNM575 were digested in 250 μl of BamHI buffer with 25 units of BamHI at 37° C. for 1 hour. The 691 bp fragment with BamHI cohesive termini was isolated from a 6 percent polyacrylamide gel and purified by procedures described above. After purification of the fragment one third of it (equivalent to 8 μg of plasmid) was digested in 100 μl of FnuDII buffer (6 mM NaCl, 6 mM Tris:HCl pH 7.4, 6 mM MgCl$_2$, 6 mM β-mercaptoethanol) with 2.5 units FnuDII for 1.5 hours at 37° C. Electrophoresis on a 6 percent polyacrylamide gel and standard recovery procedures were used to isolate a 538 bp DNA fragment containing the coding sequence for the last 175 amino acids of the gene followed by a translation stop codon.

A double stranded DNA fragment (110 in FIG. 5) was synthesized by the phosphotriester method to join the lpp promoter region with the human growth hormone coding region preceeded by a start codon and a coding region for a short peptide which defines a sequence recognized and cleaved by enterokinase. The upper strand has 90 nucleotides which includes on the 5' end the 4 nucleotide single stranded sequence produced by XbaI cleavage. The lower strand has 86 nucleotides which are complementary to the last 86 nucleotides of the upper strand. The first part of the synthetic DNA fragment follows the natural sequence of the lpp gene from the XbaI restriction site in the ribosome binding site through the translation initiating methionine codon (19 bp) and is followed by the sequence for the enterokinase cleavage site and the first 47 nucleotides of human growth hormone to the unique FnuDII site previously described.

The double stranded DNA fragment (110 in FIG. 5) has the following structure:

```
XbaI
5' CTAGAGGGTATTAATAATGTTCCCATTGGATGATGATGATAAGTTCCCAA—
      TCCCATAATTATTACAAGGGTAACCTACTACTACTATTCAAGGGTT—

CCATTCCCTTATCCAGGCTTTTTGACAACGCTATGCTCCG 3'  FnuDII
   GGTAAGGGAATAGGTCCGAAAAACTGTTGCGATACGAGGC 5'
```

The fragment was prepared by recognized phosphotriester methodology by which the following segments were prepared:

(1) CTAGAGGGTAT
(2) TAATAATGTTCC
(3) CATTGGATGAT
(4) GATGATAAGTTCC
(5) CAACCATTCCC
(6) TTATCCAGGC
(7) TTTTTGACAACG
(8) CTATGCTCCG
(9) CATTATTAATACCCT

(10) ATGGGAA
(11) CTTATCATCATCCA
(12) GGTTGGGAA
(13) GGATAAGGGAAT
(14) GTCAAAAAGCCT
(15) CGGAGCATAGCGTT

Using the above-prepared segments, the T$_4$ ligase catalyzed joining reactions were performed stepwise as described below:

(a) 5'-Unphosphorylated segment 1 was joined to 5'-phosphorylated segment 2 in the presence of 5'-phosphorylated segment 9 using T$_4$ ligase to form DNA duplex 1 [E. L. Brown, R. Belagaje, M. J. Ryan and H. G. Khorana, *Methods in Enzymology* 68, 109–151 (1979)]. The duplex was isolated by preparative gel electrophoresis on 15% polyacrylamide.

(b) 5'-Phosphorylated segment 3 was joined to 5'-phosphorylated segment 4 in the presence of 5'-phosphorylated segment 11 using T$_4$ ligase to form DNA duplex 2 which was purified by 15% polyacrylamide gel electrophoresis.

(c) 5'-Phosphorylated segment 5 was joined to 5'-phosphorylated segment 6 in the presence of 5'-phosphorylated segments 12 and 13 using T$_4$ ligase to form DNA duplex 3 which was purified by 15% polyacrylamide gel electrophoresis.

(d) 5'-Phosphorylated segment 7 was joined to 5'-phosphorylated segment 8 in the presence of 5'-phosphorylated segment 14 and 5'-unphosphorylated segment 15 using T$_4$ ligase to form DNA duplex 4 which was purified by 15% polyacrylamide gel electrophoresis.

(e) The DNA duplexes 2, 3 and 4 then were joined together by T$_4$ ligase to form DNA duplex 5 which was purified by 15% polyacrylamide gel electrophoresis.

(f) To the DNA duplex 1 then were added 5'-phosphorylated segment 10 and DNA duplex 5 in the presence of T$_4$ ligase, and the resulting DNA duplex (110 in FIG. 5) was purified by 10% polyacrylamide gel electrophoresis. This DNA duplex then was enzymatically phosphorylated using T$_4$ polynucleotide kinase and [$\gamma$-p$^{32}$]ATP by following the established procedure.

The expression plasmid was constructed by enzymatically joining 0.1 picomole (0.4 μg) plasmid vector (107 in FIG. 5), 0.025 picomoles synthetic DNA fragment (110 in FIG. 5) and 0.3 picomoles (0.08 μg) of 538 bp fragment (from 109 in FIG. 5) in 24 μl of ligation buffer using 1.5 units T$_4$ DNA ligase. After incubation for 16 hours at 4° C. the mixture was used to transform *E. coli* JA221 as previously described. Transformed colonies were selected on agar plates containing 100 μg/ml ampicillin. Plasmids from 19 colonies were prepared by the previously described Birnboim screening procedure. After digestion by restriction enzymes XbaI and BamHI followed by acrylamide gel electrophoresis 12 plasmids were found to contain the expected 628 bp fragment.

Eight of the positive plasmids were digested sequentially with XbaI and PvuII and seven of these yielded a 109 bp fragment. The sequence of one plasmid was determined by the procedure described by Maxam, A. M. and Gilbert, W., *Proc. Natl. Sci. U.S.A.* 74, 560–564 (1977) and found to be correct. The plasmid was designated pNM702 (111 in FIG. 5) and has been deposited at the Northern Regional Research Center, receiving the Accession No. NRRL B-18215. Expression of human growth hormone was detected by a standard radioimmunoassay procedure described by Twomey, S.L., et al., *Clin. Chem.* 20, 389–391 (1974). Quantitative expression was determined to be at least 2 million molecules per cell.

Met-phe-pro-leu (asp)$_4$ lys-human growth hormone was partially purified from 500 gm *E. coli* cells by extraction with 8M urea and 1 percent Triton X100. The debris was removed by centrifugation and the supernatant containing the soluble human growth hormone product was fractionated on a Whatman DE52 column. The peak fractions as determined by radioimmunoassay (RIA) were pooled and subjected to isoelectric precipitation. This material was further purified on a Whatman SE53 column. The peak fractions were determined by RIA and the material was concentrated by isoelectric precipitation or ultrafiltration.

The partially purified material was subjected to cleavage by enterokinase. Crude porcine intestine enterokinase (Miles Laboratories) was further purified by the method of Anderson, et al., *Biochemistry* 16, 3354–3360 (1977). Enterokinase was incubated with substrate, and samples were removed at intervals for examination on an isoelectric focusing gel. The starting material has an isoelectric point of 4.3 and can be seen to shift with time to a band having the isoelectric point of human growth hormone (4.91).

EXAMPLE 2

Plasmid for the Expression of Met-Phe-Pro-Leu-Asp-Asp-Asp-Asp-Lys-Bovine Growth Hormone Using the Lipoprotein Promoter of *E. coli*

Plasmid pNM702 (111 in FIG. 6), the expression plasmid for human growth hormone was used as the starting material for construction of a plasmid expressing Met-Phe-Pro-Leu-Asp-Asp-Asp-Asp-Lys-bovine growth hormone.

Plasmid pBP348 (112 in FIG. 6), described in Miller, W. L., et al., *J. Biol. Chem.* 255, 7521-7524-7524 (1980), was used as the source of two DNA fragments containing the coding sequence for a portion of the bovine growth hormone gene. The plasmid contains an 831 bp sequence coding for bovine growth hormone cloned in the PstI (5'CTGCAG3') restriction site of pBR322. As an alternative to the method described in Miller et al., the sequence for bovine growth hormone can be obtained from messenger RNA isolated from bovine pituitaries by now routine procedures described by Goodman, H. M., et al., *Methods in Enzymology* 68, 75–90 (1979).

The coding sequences for human growth hormone and bovine growth hormone are very similar and show much homology. Particularly useful in the construction of the expression plasmid for bovine growth hormone were the fragments generated by digestion with the restriction enzyme PvuII (5'CAGCTG3'). The size of the fragments produced are 497 bp in human growth hormone and 494 bp in bovine growth hormone. The corresponding restriction sites occur in the same coding frames in both sequences.

Ten micrograms of pNM702 (111 in FIG. 6) containing 3 PvuII sites per molecule are digested with 1 unit of PvuII in 200 μl of PvuII restriction buffer (60 mM NaCl, 6 mM Tris:HCl pH 7.5, 6 mM MgCl$_2$, 6 mM β-mercaptoethanol) for 10 minutes at 37° C. The reaction is stopped by heating at 65° C. for 10 minutes, and the DNA was alkaline phosphatase treated. This limited digestion procedure leads to the cleavage of one-half to two-thirds of the PvuII sites present. The fragments are separated on a one percent agarose gel and the DNA fragment (113 in FIG. 6) of the size corresponding to linear plasmid with the 497 bp PvuII fragment missing (runs slightly faster than single cut plasmid) was excised, purified and used as vector in the construction of intermediate plasmid (114 in FIG. 6).

A 494 bp PvuII fragment was prepared from pBP348. Ten micrograms of the plasmid were digested in 200 μl of PvuII buffer with 10 units of PvuII for 1 hour at 37° C. The fragments were separated on a 6 percent polyacrylamide gel and the 494 bp fragment (from 112 in FIG. 6) was visualized and purified by methods described previously.

Intermediate plasmid (114 in FIG. 6) is constructed by ligation of 0.2 μg vector with 0.05 μg of 494 bp fragment in 20 μl of T4 DNA ligase buffer containing 2 units T4 DNA ligase for 16 hours at 4° C. After transformation and selection of transformants for ampicillin resistance, plasmids prepared by the previously described Birnboim procedure are analyzed for the presence of the 494 bp PvuII fragment. Proper orientation of the fragment is determined by sequential digestion with enzymes XbaI and SmaI. The 494 bp PvuII fragment from the bovine growth hormone sequence has a unique asymetric SmaI restriction site. Parent plasmid pNM702 contains no SmaI sites. A plasmid with a 494 bp PvuII fragment and a 440 bp XbaI, SmaI fragment is selected as the desired intermediate and is used in further constructions.

Intermediate plasmid (114 in FIG. 7) is converted to the desired fused bovine growth hormone expression plasmid by two procedures: (1) the coding sequence of the first 30 amino acids of enterokinase substrate-human growth hormone was removed and replaced with the coding sequence for the first 31 amino acids of enterokinase substrate-bovine growth hormone and (2) a short sequence between the second PvuII site in the coding sequence to the stop codon (which is a human growth hormone sequence) is replaced with a synthetic fragment to restore the codon for alanine, the 190th amino acid of bovine growth hormone.

Ten micrograms of the intermediate plasmid (114 in FIG. 7) are digested with 1 unit PvuII in 200 μl PvuII buffer for 5 minutes at 37° C. The reaction is stopped by heating at 65° C. for 10 minutes. The mixture of fragments is spread on a 1 percent agarose gel and linear plasmid having only a single PvuII cut per molecule is recovered and purified. This recovered material (approximately 3 μg) is digested completely with 5 units of XbaI and treated with alkaline phosphatase. The fragments are spread on a 1 percent agarose gel and the largest fragment (missing the 109 bp fragment between XbaI and the first PvuII site in human and bovine growth hormone) is recovered and used as the cloning vector (115 in FIG. 7).

The DNA sequence for the first 23 amino acids (69 bp) of bovine growth hormone to the first PvuII site contains 2 restriction sites for enzyme HpaII (5'CCGG3'). The first site is 23 bp from the first nucleotide of the coding sequence. A 63 bp fragment (116 in FIG. 7) was synthesized by the phosphotriester method. This fragment corresponds to the 19 bp sequence from the XbaI site in the 1pp ribosome binding site through the ATG initiation codon followed by the coding sequence for Phe-Pro-Leu-Asp-Asp-Asp-Asp-Lys (24 bp) and 20 nucleotides of the coding sequence of bovine growth hormone from Phe to the first HpaII site.

The fragment has the following structure:

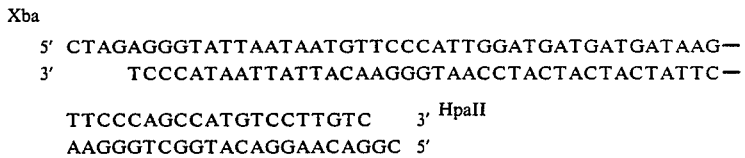

```
    Xba
5'  CTAGAGGGTATTAATAATGTTCCCATTGGATGATGATGATAAG—
3'      TCCCATAATTATTACAAGGGTAACCTACTACTACTATTC—

TTCCCAGCCATGTCCTTGTC    3'  HpaII
    AAGGGTCGGTACAGGAACAGGC  5'
```

In producing the 63 bp fragment, the following nine segments were prepared:
(1) CTAGAGGGTAT
(2) TAATAATGTTCC
(3) CATTGGATGAT
(4) GATGATAAGTTCC
(5) CAGCCATGTCCTTGTC
(6) ATGGGAACATTATTAATACCCT
(7) TTATCATCATCATCCA
(8) ATGGCTGGGAAC
(9) CGGACAAGGAC Using the above-prepared segments, the T4 ligase catalyzed joining reactions were performed stepwise as described below:
(a) 5'-Unphosphorylated segment 1 was joined to 5'-phosphorylated segment 2 in the presence of 5'-phosphorylated segment 6 using T4 ligase to form DNA duplex 1 which was purified by 15% polyacrylamide gel electrophoresis.
(b) 5'-Phosphorylated segments 3, 4 and 5 were joined in the presence of 5'-phosphorylated segments 7 and 8 and 5'-unphosphorylated segment 9 using T4 ligase to form DNA duplex 2 which was purified by 15% polyacrylamide gel electrophoresis.
(c) Duplexes 1 and 2 then were joined by T4 ligase to form DNA duplex (116 in FIG. 7) which was purified by 15% polyacrylamide gel electrophoresis. This DNA duplex then was enzymatically phosphorylated using T4 polynucleotide kinase and [γ-p$^{32}$]ATP following established procedure.

The DNA fragment of 46 bp which runs from the above described HpaII site to the PvuII site was obtained from the original pBP348 plasmid. One hundred micrograms of plasmid were digested in 400 μl of PvuII buffer with 50 units of PvuII for 2 hours at 37° C. After phenol extraction and ethanol precipitation the DNA was dissolved in 400 μl of PstI (5'CTGCAG3') buffer (50 mM NaCl, 6 mM Tris:HCl pH 7.4, 6 mM MgCl$_2$, 6 mM β-mercaptoethanol) with 50 units of PstI for 2 hours at 37° C. The DNA fragments were spread on a 6 percent polyacrylamide gel (30 cm long) and the 135 bp fragment containing the desired 46 bp sequence was recovered and purified by standard procedures. One-third of the recovered DNA (equivalent to 33 μg of plasmid) was subjected to limited digestion by HpaII restriction enzyme. The DNA was digested in 100 μl HpaII buffer (20 mM Tris:HCl pH 7.4, 7 mM MgCl$_2$, 6 mM β-mercaptoethanol) with 1 unit of HpaII for 40 minutes at 37° C. The reaction was stopped by heating at 65° C. for 10 minutes. The DNA fragments were run on a 5 percent acrylamide gel (acrylamide:bis ratio 19:1). One microgram of pBR322 digested with SauIIIA restriction enzyme was run in a separate well. This mixture of fragments contains a 46 bp fragment which is used as a size marker. The 46 bp fragment yielded by HpaII partial digestion of the 135 bp fragment (from 112 in FIG. 7) was purified by standard procedures.

Two-tenths microgram plasmid vector (115 in FIG. 7) having XbaI and PvuII ends was combined with 3.2 picomoles of synthetic 63 bp fragment (116 in FIG. 7) and 0.5–1 picomoles 46 bp fragment (from 112 in FIG. 7) in 10 μl ligation buffer with 2 units of $T_4$ DNA ligase and ligated for 16 hours at 4° C. The mixture was used to transform E. coli JA221, and plasmids were prepared from colonies selected by ampicillin resistance. The plasmids were screened for the presence of a 494 bp PvuII fragment and a 109 bp XbaI, PvuII fragment. One of twelve analyzed had these fragments. This plasmid was sequenced from the XbaI site through the PvuII site and tested in a radioimmunoassay for bovine growth hormone. It was found to respond positively in the radioimmunoassay and had the correct sequence. This plasmid was designated pNM789 (117 in FIG. 7) and has been deposited at the Northern Regional Research Center, receiving the Accession No. NRRL B-18216. Quantitative expression was measured by standard radioimmunoassay procedures for bovine growth hormone and found to be at least $10^5$ molecules per cell.

Plasmid pNM789 (117 in FIG. 8) requires one amino acid codon change for complete conversion to bovine growth hormone. This is accomplished by the removal of the 28 bp PvuII to BamHI fragment of pNM789 and replacement with a synthetic double strand fragment (13 bp upper strand, 17 bp lower strand) having the following sequence and shown at 118 in FIG. 8:

5'CTGTGCCTTCTAG3'
3'GACACGGAAGATCCTAG5'

Ten micrograms of pNM789 are digested with 1 unit of PvuII in 200 μl PvuII buffer for 5 minutes at 37° C. The enzyme is inactivated by heating 10 minutes at 65° C. The sample is diluted to 300 μl with the addition of BamHI buffer and digested to completion with 10 units of BamHI for 1 hour at 37° C. This is followed by the addition of 5 units of alkaline phosphatase and incubation for 1 hour at 65° C. The DNA fragments are separated on a 1 percent agarose gel, and a DNA fragment (119 in FIG. 8) the size of single cut plasmid is purified. Two-tenths microgram of this is ligated with 5 picomoles of synthetic fragment using 2 units of $T_4$ ligase in 20 μl ligase buffer overnight at 4° C. Following transformation and the previously described Birnboim plasmid isolation procedure, several plasmids are selected which contain the appropriate size PvuII fragment (494 bp) and XbaI, BamHI fragment (628 bp). The sequence of at least two of these is determined from the BamHI site toward the unique SmaI site and one selected with the desired sequence (120 in FIG. 8).

EXAMPLE 3

Plasmid for the Expression of Met-Phe-Pro-Leu-Asp-Asp-Asp-Asp-Lys-Bovine Growth Hormone Using the Lipoprotein Promoter in E. coli Plasmid pIMIA3 (121 in FIG. 9), which is on deposit as NRRL B-15733, contains a thermoinducible runaway replicon and the lpp promoter and ribosome binding sequences identical to those present in pNM789 (117 in FIG. 7). In addition, it confers resistance to kanamycin.

Plasmid pCC101 (124 in FIG. 9) was constructed by ligating 2 μg of CsCl gradient purified vector (pIMIA3) DNA, cleaved with XbaI and BamHI (123 in FIG. 9), and 1 μg of the small, gel-purified XbaI to BamHI fragment from plasmid 120 (122 in FIG. 8). The latter fragment contains the Met-Phe-Pro-Leu-Asp-Asp-Asp-Asp-Lys-bovine growth hormone coding region. The resulting ligation mixture (30 μl) contained 20mM Tris-HCl (pH 7.6), 10 mM dithiothreitol, 10 mM $MgCl_2$, 0.5 mM ATP, and 40 units of $T_4$ DNA ligase. The mixture was incubated for 2 hours at 23°–25° C. after which it was heated at 65° C. for 5 minutes and transformed into 200 μl of $CsCl_2$-treated JA221 cells [Wensink et al., Cell 3, 315–325 (1974)]. Transformants were selected at 30° C. on Ty agar plates containing 100 μg/ml kanamycin. The plasmids from several colonies were examined by restriction analysis using several enzymes and were shown to have the expected structure. About 10% of those shown to have the expected structure were capable of amplifying their plasmid DNA to approximately 1000 copies per cell at 37° C. These isolates, obtained as described, were designated pCC101 (124 in FIG. 9). A plasmid therefrom was transformed into E. coli RV308 and expressed using standard techniques. E. coli cells were harvested by centrifugation, and the packed cells were maintained frozen until used.

The frozen cells were thawed and suspended in 0.05 M Tris-HCl buffer, pH 8.6, in a ratio of 5 ml buffer/gram cells. To each gram of cells in the stirred, homogeneous suspension were added 2 mg egg-white lysozyme dissolved in 0.5 ml 0.05 M EDTA, pH 8.6. The suspension was allowed to stand at room temperature 15 minutes after which it was sonicated for 30 seconds. The sonication was repeated twice at 5 minute intervals. Visual examination with a phase contrast microscope confirmed that all cells had been lysed. A 50 percent slurry of Whatman "Cell Debris Remover" (CDR), a modified cellulose, was made in 0.05 M Tris-HCl buffer and adjusted to a final pH of 8.0. CDR (5 grams) in 5 ml buffer was prepared per gram of cells. About 1/5 of the slurry was used to pre-coat a Buchner funnel. The remainder was added to the lysed cell preparation, and the mixture was stirred for about one minute and added to the pre-coated filter. The filter cake was washed with 0.05 M Tris-HCl buffer, pH 8.0.

The filtrate contained the growth hormone granules which were collected by centrifugation at 5000 x g for 10 minutes. The granules were washed by suspending them in water and centrifuging as before. About 45 mg of granule protein were obtained per gram of cells.

To 3.5 liters $H_2O$ containing 3.5 ml 0.5 M Tris, 5 ml 5 N NaOH and 41.2 mg. L-cysteine was added one gram of granule protein. Upon dissolution of the granules (about 2 minutes), the pH was adjusted to 8.6–9.0 with 1 N HCl, and the mixture was stirred for 2 hours at room temperature. One gram $Na_2S_4O_6$ was added, and stirring was continued for 15 minutes. One liter (settled volume) of DEAE-cellulose, pH 8.6, was added, and the mixture was stirred 5 minutes and allowed to settle. The supernatant liquid was decanted. The cellulose was washed once by decantation with 7 liters 0.005 M Tris-HCl, pH 8.6, 0.001 M $Na_2S_4O_6$. The settled cellulose was poured into a 5×60 cm chromatography column and washed with 0.05 M Tris-HCl, pH 8.6, by gravity flow for 45 minutes. The growth hormone was eluted by pumping 0.1 M Tris-HCl buffer, pH 8.0, 0.001 M $Na_2S_4O_6$, 0.1 M NaCl through the column at 200 ml/min. The initial peak of eluted protein was collected in 400 ml and was loaded onto a 2.5×60 cm column of Phenyl-Sepharose CL-4B (Pharmacia) previously equilibrated with 0.1 M $NH_4HCO_3$. The loaded column was washed with one column volume of 0.1 M $NH_4HCO_3$, and then was eluted with 0.001 M $NH_4HCl_3$. Growth hormone eluted in about 200 ml and was freeze-dried. The final yield of pure Met-Phe-Pro-Leu-Asp-Asp-Asp-Asp-Lys-bovine growth hormone was 240 mg from 22 grams of cells.

Bioassay of Met-Phe-Pro-Leu-Asp-Asp-Asp-Asp-Lys-Bovine Growth Hormone

Met-Phe-Pro-Leu-Asp-Asp-Asp-Asp-Lys-bovine growth hormone was analyzed for biological activity using the following "Tibia Assay".

Female rats, hypophysectomized at 25 days of age, are given, in addition to rat chow, 5% glucose water ad libitum for the first 48 hours following hypophysectomy after which normal tap water is used. On the 7th day (32 days of age) after hypophysectomy animals that are obviously sick or weak are eliminated. All remaining rats are earmarked and weighed. At day 14 (39 days of age) after hypophysectomy the rats are weighed again. Rats that have gained more than 10 grams during the seven-day period and those weighing in excess of 120 grams are eliminated.

The test compound is dissolved in a minimum of 0.01 M $NaHCO_3$, pH 8.0 and then is brought to the desired final volume by addition of physiological saline (0.1 N NaCl) or distilled water.

On the 14th day after hypophysectomy (39 days of age) the animals are randomized into control and treatment groups. One group serves as control and receives vehicle only. All treatments are administered at a volume of 0.1 ml by subcutaneous injection once daily for 4 days. Individual body weights are recorded at the beginning of the assay. Approximately 18-24 hours following the fourth injection, body weights are again recorded, and the rats are sacrificed by carbon dioxide asphyxiation. The sella turcica of each rat is visually checked for completeness of hypophysectomy. The right tibia of each rat is removed, dissected free from soft tissue, and split in a midsaggittal plane with a scalpel to expose a cross-section of the proximal epiphyseal cartilage plate.

The tibias so removed and split are subjected to the following histological preparation. Bone halves are
(1) Fixed in 10 percent neutral formalin for at least 72 hours.
(2) Washed thoroughly in deionized water for one hour.
(3) Immersed in acetone for one hour.
(4) Washed again in deionized water for one hour.
(5) Immersed in 2 percent silver nitrate for exactly 2 minutes and then immediately placed in deionized water while being exposed to strong light for 6 minutes (calcified parts appear dark brown).
(6) Rapidly removed from water and submerged immediately and fixed in 10 percent sodium thiosulfate for about 30 seconds.
(7) Washed thoroughly in deionized water for 30 minutes and maintained in deionized water until reading.

Following reading, the bones are stored in 80 percent ethanol in the dark.

The width of the uncalicified epiphyseal cartilage is determined. A binocular dissecting scope with a 10x occular lens (reticle micrometer eyepiece with 0.1 mm divisions) and a 4x objective lens is used for determining the cartilage plate width. The separate readings are made across the epiphyseal plate and recorded on the data sheet. Using a scope having the above lens configuration, the width of the epiphyseal plate in micra is calculated by multiplying each value by 25 (with this lens configuration, 1 mm on a ruler is covered by 40 small divisions on the reticle; therefore, one division =25 microns). The arithmetic mean of all ten readings for each bone are calculated. The mean of all bones within a treatment group are also calculated.

Using the above method, the results depicted in the Table following were obtained. The compound Met-Phe-Pro-Leu-Asp-Asp-Asp-Asp-Lys-bovine growth hormone (Compound I) is compared against the vehicle as Control and a sample of pituitary source standard bovine growth hormone obtained from the National Pituitary Agency (Compound II).

TABLE

| Test Compound | Dose, $\mu g^a$ | No. of Rats | Proximal Tibia Epiphyseal Cartilage width, $\mu$ | Body Weight Gain, g. |
|---|---|---|---|---|
| Control | — | 7 | 146.1 ± 6.3 | 0.1 ± 1.2 |
| I | 25 | 7 | 203.9 ± 12.2 | 3.8 ± 1.3 |
| I | 50 | 7 | 302.9 ± 26.12 | 4.7 ± 1.6 |
| I | 100 | $6^b$ | 336.7 ± 4.4 | 5.5 ± 1.0 |
| II | 25 | 7 | 201.4 ± 19.6 | 1.8 ± 1.4 |
| II | 50 | $6^b$ | 276.3 ± 6.5 | 5.0 ± 0.9 |
| II | 100 | 7 | 309.6 ± 6.4 | 5.4 ± 1.1 |

$^a$Represents total amount of compound administered in four once per day doses of 0.1 ml each.
$^b$One bone eliminated due to breakage during staining procedure.

We claim:

1. A recombinant DNA cloning vector useful for expressing exogenous protein, which comprises
   (a) a DNA segment containing a functional origin of replication;
   (b) one or more DNA segments, each of which conveys to a transformable host cell a property useful for selection when said vector is transformed into said host cell; and
   (c) a DNA segment comprising a sequence that defines in tandem,
      (1) the promoter of a lipoprotein gene
      (2) the 5' untranslated region of a lipoprotein gene and
      (3) a translation start codon followed, without interposition of a portion or all of a nucleotide sequence coding for endogenous protein, by a nucleotide sequence coding for an enterokinase cleavage site said site being a sequence of amino acid residues comprising Asp-Asp-Asp-Asp-Lys, to which is joined, without interruption, a nucleotide sequence coding for an exogenous protein.

2. Cloning vector of claim 1, in which the exogenous protein nucleotide sequence codes for human growth hormone or bovine growth hormone.

3. Cloning vector of claim 1, in which the source of the nucleotide sequence of the promoter and that of the 5' untranslated region is a gram-negative bacterium.

4. Cloning vector of claim 3, in which the source of the nucleotide sequence of the promoter and that of the 5' untranslated region is the same gram-negative bacterium.

5. Cloning vector of claim 4, which contains in whole or in part the 3' untranslated region of a lipoprotein gene, said 3' untranslated region being located downstream of the sequence coding for said exogenous protein.

6. Cloning vector of claim 4, which contains in whole or in part the transcription termination region of a lipoprotein gene, said transcription termination region being located downstream of the sequence coding for said exogenous protein.

7. Cloning vector of claim 5, which contains in whole or in part the transcription termination region of a lipoprotein gene, said transcription termination region being located downstream of said 3' untranslated region.

8. Cloning vector of claim 4, in which the source of the nucleotide sequence of the promoter and that of the 5' untranslated region is $E.\ coli$.

9. Cloning vector of claim 8, in which the coding sequence for exogenous protein is for human growth hormone.

10. Cloning vector of claim 8, in which the coding sequence for exogenous protein is for bovine growth hormone.

11. Cloning vector of claim 7 in which the source of the nucleotide sequence of the promoter and that of the 5' untranslated region is $E.\ coli$.

12. Cloning vector of claim 11, in which the coding sequence for exogenous protein is for human growth hormone.

13. Cloning vector of claim 11, in which the coding sequence for exogenous protein is for bovine growth hormone.

14. Cloning vector of claim 2, in which the source of the nucleotide sequence of the promoter and that of the 5' untranslated region is a gram-negative bacterium.

15. Cloning vector of claim 14, in which the source of the nucleotide sequence of the promoter and that of the 5' untranslated region is the same gram-negative bacterium.

16. Cloning vector of claim 15, which contains in whole or in part the 3' untranslated region of a lipoprotein gene, said 3' untranslated region being located downstream of the sequence coding for said exogenous protein.

17. Cloning vector of claim 16, which contains in whole or in part the transcription termination region of a lipoprotein gene, said transcription termination region being located downstream of said 3' untranslated region.

18. Cloning vector of claim 17, in which the source of the nucleotide sequence of the promoter and that of the 5' untranslated region is $E.\ coli$.

19. Cloning vector of claim 1, in which the DNA sequence coding for the enterokinase cleavage site comprises

GATGATGATGATAAG
CTACTACTACTATTC.

20. Cloning vector of claim 19, in which the enterokinase cleavage site codes for Phe-Pro-Leu-Asp-Asp-Asp-Asp-Lys.

21. Cloning vector of claim 20, in which the DNA sequence coding for the enterokinase cleavage site is

TTCCCATTGGATGATGATGATAAG
AAGGGTAACCTACTACTACTATTC.

22. Plasmid pNM702.

23. Plasmid pNM789.

24. DNA sequence of the formula

5' CTAGAGGGTATTAATAATGTTCCCATTGGATGATGATGATAAGTTCCCAA—
3'     TCCCATAATTATTACAAGGGTAACCTACTACTACTATTCAAGGGTT—

CCATTCCCTTATCCAGGCTTTTTGACAACGCTATGCTCCG 3'
GGTAAGGGAATAGGTCCGAAAAACTGTTGCGATACGAGGC 5'.

25. DNA sequence of the formula

CTAGAGGGTATTAATAATGTTCCCATTGGATGATGATGATAAG—
TCCCATAATTATTACAAGGGTAACCTACTACTACTATTC—

TTCCCAGCCATGTCCTTGTC    3'
AAGGGTCGGTACAGGAACAGGC  5'.

26. DNA sequence of the formula

TTCCCATTGGATGATGATGATAAG
AAGGGTAACCTACTACTACTATTC.

* * * * *